United States Patent
Kim et al.

[11] Patent Number: 6,051,737
[45] Date of Patent: Apr. 18, 2000

[54] ARYL BENZOYL UREA DERIVATIVE AND PESTICIDAL COMPOSITION COMPRISING THE SAME

[75] Inventors: Jung Ho Kim, Taejon; Je Wan Woo; Yong Woo Shin, both of Seoul; Jung Nyoung Heo, Taejeon; Eui Deok Kim, Taejeon; Joon Seo Park, Taejeon, all of Rep. of Korea

[73] Assignee: Dongbu Hannong Chemical, Co. Ltd., Seoul, Rep. of Korea

[21] Appl. No.: 09/091,760
[22] PCT Filed: Nov. 7, 1996
[86] PCT No.: PCT/KR96/00196
 § 371 Date: Aug. 26, 1998
 § 102(e) Date: Aug. 26, 1998
[87] PCT Pub. No.: WO97/24321
 PCT Pub. Date: Jul. 10, 1997

[30] Foreign Application Priority Data

Dec. 27, 1995 [KR] Rep. of Korea ............ 95/72367

[51] Int. Cl.$^7$ ................................. C07C 273/00
[52] U.S. Cl. ................................. 564/44
[58] Field of Search ................................. 564/44

[56] References Cited

U.S. PATENT DOCUMENTS

| 4,110,469 | 8/1978 | Wellinga et al. ............ 514/522 |
| 4,166,124 | 8/1979 | Wellinga et al. ............ 514/389 |
| 4,918,227 | 4/1990 | Becher et al. ............ 564/44 |
| 5,245,071 | 9/1993 | Wellinga et al. ............ 560/27 |

FOREIGN PATENT DOCUMENTS

| 0232080A2 | 8/1987 | European Pat. Off. . |
| 2168702A | 6/1986 | United Kingdom . |
| WO 9533711 | 12/1995 | WIPO . |

*Primary Examiner*—James O. Wilson
*Attorney, Agent, or Firm*—Birch, Stewart, Kolasch & Birch, LLP

[57] ABSTRACT

The present invention relates to a novel aryl benzoyl urea derivative represented by formula (I), in which $X^1$ and $X^2$ independently of one another represent hydrogen, fluoro, chloro or bromo, $R^1$ represents chloro, bromo or trifluoromethyl, one of $R^2$ and $R^4$ is hydrogen and the other represents fluoro, chloro, bromo, cyano or trifluoromethyl, and $R^3$ represents fluoro, chloro, bromo or cyano, which has a potent growth-retarding activity against pests.

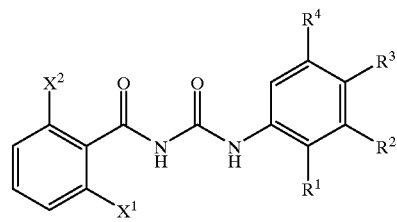

(I)

5 Claims, No Drawings

ARYL BENZOYL UREA DERIVATIVE AND PESTICIDAL COMPOSITION COMPRISING THE SAME

This application claims the benefit under 35 U.S.C. §371 of prior PCT International Application No. PCT/KR96/00196 which has an International filing date of Nov. 7, 1996 which designated the United States of America, the entire contents of which are hereby incorporated by references.

TECHNICAL FIELD

The present invention relates to a novel aryl benzoylurea derivative having a potent growth-retarding activity against pests. More specifically, the present invention relates to a novel aryl benzoylurea derivative represented by the following formula (I):

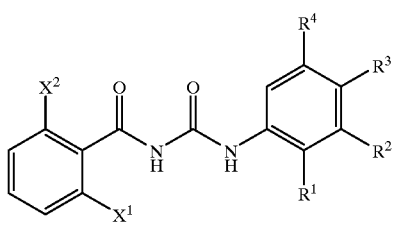

(I)

in which
- $X^1$ and $X^2$ independently of one another represent hydrogen, fluoro, chloro or bromo,
- $R^1$ represents chloro, bromo or trifluoromethyl,
- one of $R^2$ and $R^4$ is hydrogen and the other represents fluoro, chloro, bromo, cyano or trifluoromethyl, and
- $R^3$ represents fluoro, chloro, bromo or cyano.

The present invention also relates to a process for preparing the compound of formula (I), as defined above, and a pesticidal composition comprising the compound of formula (I) as an active ingredient.

BACKGROUND ART

Before the present invention, several kinds of benzoyl urea compounds have been developed as an inhibitor for chitin formation. As typical examples commercially available, N-(2,6-difluorobenzoyl)-N'-(4-chlorophenyl)urea described in U.S. Pat. No. 3,933,908 and N-(2,6-difluorobenzoyl)-N'-(3,4-dichlorophenyl)urea described in U.S. Pat. No. 4,166,124 can be mentioned, which were the initiation of the developments of benzoyl urea-based pesticides.

European Patent Publication Nos. 093,976 and 093,977 disclose aryl benzoyl urea derivatives having a similar structure to the desired compound of the present invention. However, they are different from the compound (I) of the present invention in that all the substituents of $R^2$, $R^3$ and $R^4$ are some groups other than hydrogen, or $R^3$ position is substituted with an ether group. Furthermore, their pesticidal spectrum is restricted to Plutella. And compounds with good pesticidal activity among them are mainly benzoyl ureido diphenyl ether derivatives, which can be prepared only through complicated and uneconomic processes.

In addition, European Patent Publication No. 232,080 discloses benzoyl urea derivative of which aryl moiety is 2,5-difluoro-4-chlorophenyl. However, since $LC_{50}$ thereof against Spodoptera is 0.3 to 0.4 ppm, it has a much lower activity than the compound according to the present invention having 0.1 ppm or less of $LC_{50}$ against the same pest.

While, International Patent Application No. PCT/KR95/00072, which was filed by the present applicant, discloses phenyl benzoyl(nicotinoyl) urea derivatives wherein $R^3$ position is fixedly substituted with hydrogen, which is different from the compound of the present invention wherein $R^3$ position is substituted with halogen or cyano. Further, with respect to the pesticidal activity against both Plutella xylostella and Spodoptera litura, the compound of the present invention is superior to that described in the International Patent Appln. No. PCT/KR95/00072.

DISCLOSURE OF INVENTION

The present inventors have extensively studied to develop a novel aryl benzoyl urea derivative which can be prepared by a convenient process and as well exhibits a superior pesticidal activity even at a low concentration. As a result of such studies, we have identified that an aryl benzoyl urea derivative of the formula (I) above has never been disclosed in any prior publications and can satisfy such requirements, and thus completed the present invention.

Accordingly, it is an object of the present invention to provide a novel aryl benzoyl urea derivative represented by the following formula (I):

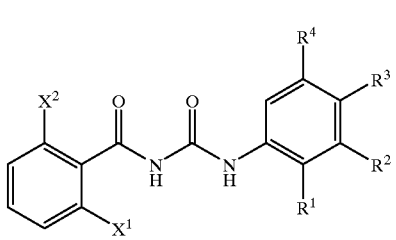

(I)

in which
- $X^1$ and $X^2$ independently of one another represent hydrogen, fluoro, chloro or bromo,
- $R^1$ represents chloro, bromo or trifluoromethyl,
- one of $R^2$ and $R^4$ is hydrogen and the other represents fluoro, chloro, bromo, cyano or trifluoromethyl, and
- $R^3$ represents fluoro, chloro, bromo or cyano.

It is another object of the present invention to provide a process for preparing the novel aryl benzoyl urea derivative of formula (I):

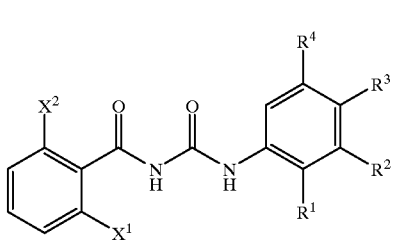

(I)

in which
- $X^1$ and $X^2$ independently of one another represent hydrogen, fluoro, chloro or bromo,
- $R^1$ represents chloro, bromo or trifluoromethyl,
- one of $R^2$ and $R^4$ is hydrogen and the other represents fluoro, chloro, bromo, cyano or trifluoromethyl, and
- $R^3$ represents fluoro, chloro, bromo or cyano, characterized in that a benzoyl isocyanate having the following formula (II):

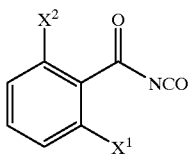

(II)

in which
X¹ and X² are defined as previously described, is reacted with an aniline derivative having the following formula (III):

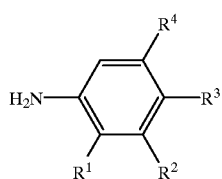

(III)

in which
R¹, R², R³ and R⁴ are defined as previously described in the presence of a diluent.

It is a further object of the present invention to provide a pesticidal composition comprising the aryl benzoyl urea derivative of formula (I) as an active ingredient, in combination with an agriculturally acceptable carrier.

BEST MODE FOR CARRYING OUT THE INVENTION

In one aspect, the present invention relates to a novel aryl benzoyl urea derivative having the following formula (I), which has a potent pesticidal activity:

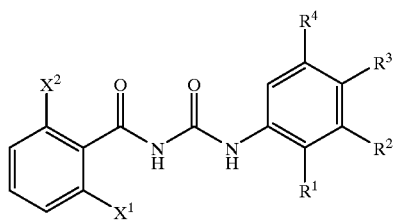

(I)

in which
X¹ and X² independently of one another represent hydrogen, fluoro, chloro or bromo,
R¹ represents chloro, bromo or trifluoromethyl,
one of R² and R⁴ is hydrogen and the other represents fluoro, chloro, bromo, cyano or trifluoromethyl, and
R³ represents fluoro, chloro, bromo or cyano.

Among the compound of formula (I) according to the present invention, the preferred one includes those wherein X¹ and X² independently of one another represent hydrogen, fluoro or chloro, R¹ represents chloro, bromo or trifluoromethyl, one of R² and R⁴ is hydrogen and the other represents chloro, bromo or trifluoromethyl, and R³ represents fluoro, chloro, bromo or cyano.

Typical examples of the compound of formula (I) according to the present invention are as follows:
1-(2-bromo-4-chloro-5-trifluoromethylphenyl)-3-(2,6-difluorobenzoyl)urea;
1-(2-bromo-4-chloro-5-trifluoromethylphenyl)-3-(2-fluorobenzoyl)urea;
1-(2-bromo-4-chloro-5-trifluoromethylphenyl)-3-(2-chlorobenzoyl)urea;
1-(2-bromo-4-chloro-5-trifluoromethylphenyl)-3-(2-bromobenzoyl)urea;
1-(4,5-dibromo-2-trifluoromethylphenyl)-3-(2,6-difluorobenzoyl)urea;
1-(4,5-dibromo-2-trifluoromethylphenyl)-3-(2,6-dichlorobenzoyl)urea;
1-(2,4-dibromo-5-trifluoromethylphenyl)-3-(2,6-difluorobenzoyl)urea;
1-(2,4-dibromo-5-trifluoromethylphenyl)-3-(2-chlorobenzoy)urea;
1-(2,4-dibromo-5-trifluoromethylphenyl)-3-(2-fluorobenzoyl)urea;
1-(2-bromo-5-chloro-4-cyanophenyl)-3-(2,6-difluorobenzoyl)urea;
1-(2-bromo-4-fluoro-5-trifluoromethylphenyl)-3-(2,6-difluorobenzoyl)urea;
1-(2-bromo-4-fluoro-5-trifluoromethylphenyl)-3-(2-fluorobenzoyl)urea;
1-(2-bromo-4-fluoro-5-trifluoromethylphenyl)-3-(2-chlorobenzoyl)urea;
1-(2-chloro-4-fluoro-5-trifluoromethylphenyl)-3-(2,6-difluorobenzoyl)urea;
1-(2-chloro-4-fluoro-3-trifluoromethylphenyl)-3-(2,6-difluorobenzoyl)urea;
1-(2-chloro-4-fluoro-3-trifluoromethylphenyl)-3-(2-fluorobenzoyl)urea;
1-(2-chloro-4-fluoro-3-trifluoromethylphenyl)-3-(2-chlorobenzoyl)urea;
1-(2-chloro-4-fluoro-3-trifluoromethylphenyl)-3-(2,6-dichlorobenzoyl)urea;
1-(2,3-dichloro-4-cyanophenyl)-3-(2,6-difluorobenzoyl)urea;
1-(2,3-dichloro-4-cyanophenyl)-3-(2-fluorobenzoyl)urea;
1-(2,3-dichloro-4-cyanophenyl)-3-(2-chlorobenzoyl)urea;
1-(2,5-dichloro-4-cyanophenyl)-3-(2,6-difluorobenzoyl)urea;
1-(2,5-dichloro-4-cyanophenyl)-3-(2-chlorobenzoyl)urea;

In another aspect, the present invention relates to a process for preparing the compound of formula (I) as defined above.

According to the process of the present invention, the desired aryl benzoyl urea derivative of formula (I) can be prepared by reacting a benzoyl isocyanate of formula (II) with an aniline derivative of formula (III) in a suitable diluent, as shown in the following reaction scheme:

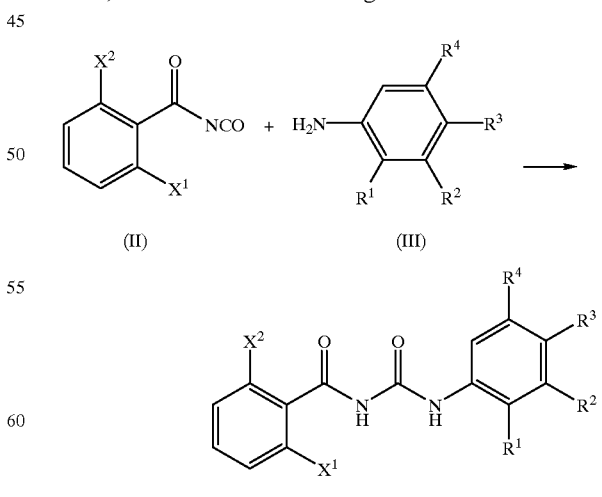

In the above reaction scheme, X¹, X², R¹, R², R³ and R⁴ are defined as previously described.

The reaction of the compound of formula (II) with the compound of formula (III) according to the present invention can be carried out in the presence of a diluent. For this purpose, any inert organic solvent can be used unless it adversely affect the reaction. Particularly, the diluent which can be preferably used in this reaction includes optionally chlorinated aliphatic or aromatic hydrocarbons such as benzene, toluene, xylene, methylene chloride, chloroform, carbon tetrachloride, 1,2-dichloroethane, tetrahydrofuran or chlorobenzene; ethers such as diethyl ether, dibutyl ether or dioxane; ketones such as acetone, methyl ethyl ketone, methyl isopropyl ketone or methyl isobutyl ketone; and nitriles such as acetonitrile or propionitrile, and the like. The reaction can be generally carried out at the temperature of 0 to 1200° C., preferably 10 to 50° C., under room pressure.

In this reaction, the reactants are preferably used in an equimolar amount. Although any one of the reactants can be used in an excessive amount, it is not advantageous in view of economics in either industrial scale or laboratory.

The aryl benzoyl urea compound of formula (I) is prepared by stirring the reactants for 2 hours or more in the inert diluent as mentioned above at the temperature as defined above and then filtering the resulting product in vacuo. All the products thus obtained are present in the form of a crystal, have definite melting points, and are identified by NMR spectrum.

The benzoyl isocyanate compound of formula (II) used in the above reaction as a starting material can be prepared by reacting the substituted benzamide represented by the following formula (IV) with an oxalyl chloride in the presence of an organic solvent. As the organic solvent, benzene, toluene, xylene, chlorobenzene or 1,2-dichloroethane can be used, and the reaction should be proceeded until no more gases are generated.

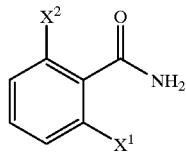

(IV)

in which, $X^1$ and $X^2$ are defined as previously described.

Typical examples of the novel aryl benzoyl urea derivative of formula (I) prepared according to the present invention are listed in the following table 1.

TABLE 1

| COM. No. | $X^1$ & $X^2$ | $R^1$ | $R^2$ | $R^3$ | $R^4$ | M.P. (° C.) |
|---|---|---|---|---|---|---|
| 1 | 2,6-$F_2$ | Br | H | Cl | $CF_3$ | 196 |
| 2 | 2-F | Br | H | Cl | $CF_3$ | 170 |
| 3 | 2-Cl | Br | H | Cl | $CF_3$ | 185 |
| 4 | 2-Br | Br | H | Cl | $CF_3$ | 193 |
| 5 | 2,6-$F_2$ | $CF_3$ | H | Br | Br | 203 |
| 6 | 2,6-$Cl_2$ | $CF_3$ | H | Br | Br | 204 |
| 7 | 2,6-$F_2$ | Br | H | Br | $CF_3$ | 197 |
| 8 | 2-Cl | Br | H | Br | $CF_3$ | 191 |
| 9 | 2-F | Br | H | Br | $CF_3$ | 181 |
| 10 | 2,6-$F_2$ | Br | H | CN | Cl | 247 |
| 11 | 2,6-$F_2$ | Br | H | F | $CF_3$ | 181 |
| 12 | 2-F | Br | H | F | $CF_3$ | 171 |
| 13 | 2-Cl | Br | H | F | $CF_3$ | 192 |
| 14 | 2,6-$F_2$ | Cl | H | F | $CF_3$ | 192 |
| 15 | 2,6-$F_2$ | Cl | $CF_3$ | F | H | 214 |
| 16 | 2-F | Cl | $CF_3$ | F | H | 173 |
| 17 | 2-Cl | Cl | $CF_3$ | F | H | 208 |
| 18 | 2,6-$Cl_2$ | Cl | $CF_3$ | F | H | 227–230 |

TABLE 1-continued

| COM. No. | $X^1$ & $X^2$ | $R^1$ | $R^2$ | $R^3$ | $R^4$ | M.P. (° C.) |
|---|---|---|---|---|---|---|
| 19 | 2,6-$F_2$ | Cl | Cl | CN | H | 285–287 |
| 20 | 2-F | Cl | Cl | CN | H | 298–300 |
| 21 | 2-Cl | Cl | Cl | CN | H | 278–282 |
| 22 | 2,6-$F_2$ | Cl | H | CN | Cl | 238–240 |
| 23 | 2-Cl | Cl | H | CN | Cl | 244–247 |

The compound according to the present invention as mentioned above can be effectively used as a pesticide in agricultural field. Particularly, the compound of the present invention combats the pest through a mechanism to inhibit a chitin synthesis which results in the inhibition of peeling off the insect skin, and therefore, is less toxic to mammals. The compound of the present invention can also be utilized for protection of farm lands, forests, stored goods, and the like. It is generally active against not only sensitive or resistant species but also inserts under all the growth stages.

The present invention will be more specifically explained by the following examples. However, it should be understood that the examples are intended to illustrate and not to limit the scope of the present invention in any manner.

EXAMPLE 1

Preparation of 1-(2-bromo-4-chloro-5-trifluoromethylphenyl)-3-(2,6-difluorobenzoyl)urea 0.49 g (3.1 mmol) of 2,6-difluorobenzamide and 0.43 g (3.4 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.85 g (3.1 mmol) of 2-bromo-4-chloro-5-trifluoromethyl aniline were successively added thereto, reacted for 2 hours and filtered to obtain 0.82 g (Yield 76%) of the title compound as a solid.

M.P.: 196° C.

$^1$H-NMR (DMSO-$d_6$, 300 MHz, ppm): δ 11.94(s,1H), 10.94 (s,1H), 8.68(s,1H), 8.16(s,1H), 7.70–7.60(m,1H), 7.29–7.23(t,2H).

EXAMPLE 2

Preparation of 1-(2-bromo-4-chloro-5-trifluoromethylphenyl)-3-(2-fluorobenzoyl)urea 0.43 g (3.1 mmol) of 2-fluorobenzamide and 0.43 g (3.4 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-fluorobenzoyl isocyanate in an oily state. 10 ml of fresh 1,2-dichloroethane and 0.85 g (3.1 mmol) of 2-bromo-4-chloro-5-trifluoromethyl aniline were successively added thereto, reacted for 2 hours and filtered to obtain 0.82 g (Yield 60%) of the title compound as a solid.

M.P.: 170° C.

$^1$H-NMR (DMSO-$d_6$, 300 MHz, ppm): δ 11.50(s, 1H), 11.25 (s,1H), 8.73(s,1H), 8.16(s,1H), 7.74–7.62(m,2H), 7.39–7.32(m, 2H).

EXAMPLE 3

Preparation of 1-(2-bromo-4-chloro-5-trifluoromethylphenyl)-3-(2-chlorobenzoyl)urea 0.39 g (2.5 mmol) of 2-chlorobenzamide and 0.38 g (3.0 mmol, 1.2 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-chlorobenzoyl isocyanate in an oily state. 10 ml of fresh 1,2-dichloroethane and 0.69 g (2.5 mmol) of 2-bromo-4-chloro-5-trifluoromethyl aniline were successively added thereto, reacted for 2 hours and filtered to obtain 0.61 g (Yield 53%) of the title compound as a solid.

M.P.: 185° C.

$^1$H-NMR (DMSO-$d_6$, 300 MHz, ppm): δ 11.68(s,1H), 11.19 (s,1H), 8.74(s,1H), 8.17(s,$_1$H), 7.65–7.44(m,4H).

EXAMPLE 4

Preparation of 1-(2-bromo-4-chloro-5-trifluoromethylphenyl)-3-(2-bromobenzoyl)urea 0.47 g (2.3 mmol) of 2-bromobenzamide and 0.34 g (2.7 mmol, 1.2 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-bromobenzoyl isocyanate in an oily state. 10 ml of fresh 1,2-dichloroethane and 0.64 g (2.3 mmol) of 2-bromo-4-chloro-5-trifluoromethyl aniline were successively added thereto, reacted for 2 hours and filtered to obtain 0.25 g (Yield 22%) of the title compound as a solid.

M.P.: 193° C.

$^1$H-NMR (DMSO-$d_6$, 300 MHz, ppm): δ 11.66(s,1H), 11.18 (s,1H), 8.75(s,1H), 8.19(s,1H), 7.75–7.44(m,4H).

EXAMPLE 5

Preparation of 1-(4,5-dibromo-2-trifluoromethylphenyl)-3-(2,6-difluorobenzoyl)urea 0.34 g (2.2 mmol) of 2,6-difluorobenzamide and 0.33 g (2.6 mmol, 1.2 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.69 g (2.2 mmol) of 4,5-dibromo-2-trifluoromethyl aniline were successively added thereto, reacted for 2 hours and filtered to obtain 0.61 g (Yield 56%) of the title compound as a solid.

M.P.: 203° C.

$^1$H-NMR (DMSO-$d_6$, 300 MHz, ppm): δ 11.64(s,1H), 9.91 (s,1H), 8.39(s,1H), 8.03(s,1H), 7.69–7.59(m,1H), 7.29–7.23(t,2H).

EXAMPLE 6

Preparation of 1-(4,5-dibromo-2-trifluoromethylphenyl)-3-(2,6-dichlorobenzoyl)urea 0.51 g (2.7 mmol) of 2,6-dichlorobenzamide and 0.41 g (3.2 mmol, 1.2 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-dichlorobenzoyl isocyanate in an oily state. 10 ml of fresh 1,2-dichloroethane and 0.86 g (2.7 mmol) of 4,5-dibromo-2-trifluoromethyl aniline were successively added thereto, reacted for 2 hours and filtered to obtain 0.28 g (Yield 43%) of the title compound as a solid.

M.P.: 204° C.

$^1$H-NMR (DMSO-$d_6$, 300 MHz, ppm): δ 11.63(s,1H), 9.98 (s,1H), 8.39(s,1H), 8.03(s,1H), 7.61–7.51(m,3H).

EXAMPLE 7

Preparation of 1-(2,4-dibromo-5-trifluoromethylphenyl)-3-(2,6-difluorobenzoyl)urea 0.47 g (3.0 mmol) of 2,6-difluorobenzamide and 0.40 g (3.2 mmol, 1.05 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.95 g (3.0 mmol) of 2,4-dibromo-5-trifluoromethyl aniline were successively added thereto, reacted for 2 hours and filtered to obtain 1.15 g (Yield 76%) of the title compound as a solid.

M.P.: 197° C.

$^1$H-NMR (DMSO-$d_6$, 300 MHz, ppm): δ 11.95(s,1H), 10.95 (s,1H), 8.71(s,1H), 8.33(s,1H), 7.72–7.62(m,1H), 7.32–7.26(t,2H).

EXAMPLE 8

Preparation of 1-(2,4-dibromo-5-trifluoromethylphenyl)-3-(2-chlorobenzoyl)urea 0.47 g (3.0 mmol) of 2-chlorobenzamide and 0.40 g (3.2 mmol, 1.05 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-chlorobenzoyl isocyanate in an oily state. 10 ml of fresh 1,2-dichloroethane and 0.95 g (3.0 mmol) of 2,4-dibromo-5-trifluoromethyl aniline were successively added thereto, reacted for 2 hours and filtered to obtain 1.2 g (Yield 80%) of the title compound as a solid.

M.P.: 191° C.

$^1$H-NMR (DMSO-$d_6$, 300 MHz, ppm): δ 11.68(s,1H), 11.20 (s,1H), 8.77(s,1H), 8.33(s,1H), 7.67–7.45(m,4H).

EXAMPLE 9

Preparation of 1-(2,4-dibromo-5-trifluoromethylphenyl)-3-(2-fluorobenzoyl)urea 0.47 g (3.0 mmol) of 2-fluorobenzamide and 0.40 g (3.2 mmol, 1.05 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-fluorobenzoyl isocyanate in an oily state. 10 ml of fresh 1,2-dichloroethane and 0.95 g (3.0 mmol) of 2,4-dibromo-5-trifluoromethyl aniline were successively added thereto, reacted for 2 hours and filtered to obtain 1.11 g (Yield 77%) of the title compound as a solid.

M.P.: 181° C.

$^1$H-NMR (DMSO-$d_6$, 300 MHz, ppm): δ11.53(s,1H), 11.26 (s,1H), 8.77(s,1H), 8.33(s,1H), 7.76–7.63(m,2H), 7.42–7.34(m,2H).

EXAMPLE 10

Preparation of 1-(2-bromo-5-chloro-4-cyanophenyl)-3-(2,6-difluorobenzoyl)urea 0.27 g (1.7 mmol) of 2,6-difluorobenzamide and 0.22 g (1.9 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.40 g (1.7 mmol) of 2-bromo-5-chloro-4-cyano aniline were successively added thereto, reacted for 2 hours and filtered to obtain 0.54 g (Yield 76%) of the title compound as a solid.

M.P.: 247° C.

$^1$H-NMR (DMSO-$d_6$, 300 MHz, ppm): δ 12.07(s,1H), 11.13 (s,1H), 8.57(s,1H), 8.47(s,1H), 7.73–7.63(m,1H), 7.32–7.26(t,2H).

EXAMPLE 11

Preparation of 1-(2-bromo-4-fluoro-5-trifluoromethylphenyl)-3-(2,6-difluorobenzoyl)urea 0.43 g (2.7 mmol) of 2,6-difluorobenzamide and 0.36 g (2.9 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.7 g (2.7 mmol) of 2-bromo-4-fluoro-5-trifluoromethyl aniline were successively added thereto, reacted for 2 hours and filtered to obtain 1.05 g (Yield 88%) of the title compound as a solid.

M.P.: 181° C.

$^1$H-NMR (DMSO-$d_6$, 300 MHz, ppm): δ 11.88(s,1H), 10.81 (s,1H), 8.56(s,1H), 8.13–8.09(d,1H), 7.71–7.61(m,1H), 7.31–7.26 (t,2H).

EXAMPLE 12

Preparation of 1-(2-bromo-4-fluoro-5-trifluoromethylphenyl)-3-(2-fluorobenzoyl)urea 0.38 g (2.7 mmol) of 2-fluorobenzamide and 0.36 g (2.9 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-fluorobenzoyl isocyanate in an oily state. 10 ml of fresh 1,2-dichloroethane and 0.7 g (2.7 mmol) of 2-bromo-4-fluoro-5-trifluoromethyl aniline were successively added thereto, reacted for 2 hours and filtered to obtain 1.06 g (Yield 93%) of the title compound as a solid.

M.P.: 171° C.

$^1$H-NMR (DMSO-$d_6$, 300 MHz, ppm): δ 11.48(s,1H), 11.15 (s,1H), 8.63–8.61(d,1H), 8.12–8.09(d,1H), 7.76–7.63 (m,2H), 7.41–7.33(q,2H).

EXAMPLE 13

Preparation of 1-(2-bromo-4-fluoro-5-trifluoromethylphenyl)-3-(2-chlorobenzoyl)urea 0.42 g (2.7 mmol) of 2-chlorobenzamide and 0.36 g (2.9 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-chlorobenzoyl isocyanate in an oily state. 10 ml of fresh 1,2-dichloroethane and 0.7 g (2.7 mmol) of 2-bromo-4-fluoro-5-trifluoromethyl aniline were successively added thereto, reacted for 2 hours and filtered to obtain 1.0 g (Yield 84%) of the title compound as a solid.

M.P.: 192° C.

$^1$H-NMR (DMSO-$d_6$, 300 MHz, ppm): δ 11.76(s,1H), 10.94 (s,1H), 8.62–8.57(m,2H), 8.17–8.10(m,2H), 7.61–7.57(q,1H).

EXAMPLE 14

Preparation of 1-(2-chloro-4-fluoro-5-trifluoromethylphenyl)-3-(2,6-difluorobenzoyl)urea 0.16 g (1.0 mmol) of 2,6-difluorobenzamide and 0.14 g (1.1 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.2 g (1.0 mmol) of 2-chloro-4-fluoro-5-trifluoromethyl aniline were successively added thereto, reacted for 2 hours and filtered to obtain 0.29 g (Yield 73%) of the title compound as a solid.

M.P.: 192° C.

$^1$H-NMR (DMSO-$d_6$, 300 MHz, ppm): δ 11.90(s,1H), 10.87 (s,1H), 8.60(s,1H), 8.03–7.99(d,1H), 7.71–7.61(m,1H), 7.31–7.26(t,2H).

EXAMPLE 15

Preparation of 1-(2-chloro-4-fluoro-3-trifluoromethylphenyl)-3-(2,6-difluorobenzoyl)urea 0.25 g (1.6 mmol) of 2,6-difluorobenzamide and 0.22 g (1.8 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.3 g (1.6 mmol) of 2-chloro-4-fluoro-3-trifluoromethyl aniline were successively added thereto, reacted for 2 hours and filtered to obtain 0.45 g (Yield 73%) of the title compound as a solid.

M.P.: 214° C.

$^1$H-NMR (DMSO-$d_6$, 300 MHz, ppm): δ 11.85(s,1H), 10.81 (s,1H), 8.47(s,1H), 7.71–7.54(m,2H), 7.31–7.25(t,2H).

EXAMPLE 16

Preparation of 1-(2-chloro-4-fluoro-3-trifluoromethylphenyl)-3-(2-fluorobenzoyl)urea 0.22 g (1.6 mmol) of 2-fluorobenzamide and 0.22 g (1.8 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-fluorobenzoyl isocyanate in an oily state. 10 ml of fresh 1,2-dichloroethane and 0.3 g (1.6 mmol) of 2-chloro-4-fluoro-3-trifluoromethyl aniline were successively added thereto, reacted for 2 hours and filtered to obtain 0.42 g (Yield 67%) of the title compound as a solid.

M.P.: 173° C.

$^1$H-NMR (DMSO-$d_6$, 300 MHz, ppm): δ 11.45(s,1H), 11.16 (s,1H), 8.53(s,1H), 7.77–7.55(m,3H), 7.41–7.33(m,2H).

EXAMPLE 17

Preparation of 1-(2-chloro-4-fluoro-3-trifluoromethylphenyl)-3-(2-chlorobenzoyl)urea 0.25 g (1.6 mmol) of 2-chlorobenzamide and 0.22 g (1.8 mol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-chlorobenzoyl isocyanate in an oily state. 10 ml of fresh 1,2-dichloroethane and 0.3 g (1.6 mmol) of 2-chloro-4-fluoro-3-trifluoromethyl aniline were successively added thereto, reacted for 2 hours and filtered to obtain 0.53 g (Yield 84%) of the title compound as a solid.

M.P.: 208° C.

$^1$H-NMR (DMSO-$d_6$, 300 MHz, ppm): δ 11.60(s,1H), 11.08 (s,1H), 8.53(s,1H), 7.67–7.45(m,5H).

EXAMPLE 18

Preparation of 1-(2-chloro-4-fluoro-3-trifluoromethylphenyl)-3-(2,6-dichlorobenzoyl)urea 0.30 g (1.6 mmol) of 2,6-dichlorobenzamide and 0.22 g (1.8 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-dichlorobenzoyl isocyanate in an oily state. 10 ml of fresh 1,2-dichloroethane and 0.3 g (1.6 mmol) of 2-chloro-4-fluoro-3-trifluoromethyl aniline were successively added thereto, reacted for 2 hours and filtered to obtain 0.58 g (Yield 84%) of the title compound as a solid.

M.P.: 227–230° C.

$^1$H-NMR (DMSO-$d_6$, 300 MHz, ppm): δ 11.93(s,1H), 10.94 (s,1H), 8.51(s,1H), 7.62–7.52(m,5H).

EXAMPLE 19

Preparation of 1-(2,3-dichloro-4-cyanophenyl)-3-(2,6-difluorobenzoyl)urea 0.24 g (1.5 mmol) of 2,6-difluorobenzamide and 0.19 g (1.6 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.3 g (1.5 mmol) of 2,3-dichloro-4-cyano aniline were successively added thereto, reacted for 2 hours and filtered to obtain 0.41 g (Yield 73%) of the title compound as a solid.

M.P.: 285–287° C.

$^1$H-NMR (DMSO-$d_6$, 300 MHz, ppm): δ 12.04(s,1H), 11.22 (s,1H), 8.48–8.45(d,1H), 8.02–8.00(d,1H), 7.70–7.65 (m,1H), 7.32–7.26(t,2H).

EXAMPLE 20

Preparation of 1-(2,3-dichloro-4-cyanophenyl)-3-(2-fluorobenzoyl)urea 0.24 g (1.5 mmol) of 2-fluorobenzamide and 0.19 g (1.6 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-fluorobenzoyl isocyanate in an oily state. 10 ml of fresh 1,2-dichloroethane and 0.28 g (1.5 mmol) of 2,3-dichloro-4-cyano aniline were successively added thereto, reacted for 2 hours and filtered to obtain 0.41 g (Yield 73%) of the title compound as a solid.

M.P.: 298–300° C.

$^1$H-NMR (DMSO-$d_6$, 300 MHz, ppm): δ 11.56(s,1H), 11.28 (s,1H), 8.53–8.50(d,1H), 8.03–8.00(d,1H), 7.77–7.62 (M,2H), 7.42–7.33(m,2H).

EXAMPLE 21

Preparation of 1-(2,3-dichloro-4-cyanophenyl)-3-(2-chlorobenzoyl)urea 0.23 g (1.5 mmol) of 2-chlorobenzamide and 0.19 g (1.6 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-chlorobenzoyl isocyanate in an oily state. 10 ml of fresh 1,2-dichloroethane and 0.28 g (1.5 mmol) of 2,3-dichloro-4-cyano aniline were successively added thereto, reacted for 2 hours and filtered to obtain 0.25 g (Yield 45%) of the title compound as a solid.

M.P.: 278–282° C.

$^1$H-NMR (DMSO-$d_6$, 300 MHz, ppm): δ 11.79(s,1H), 11.48 (s,1H), 8.52–8.49(d,1H), 8.03–8.00(d,1H), 7.68–7.45 (m,4H).

EXAMPLE 22

Preparation of 1-(2,5-dichloro-4-cyanophenyl)-3-(2,6-difluorobenzoyl)urea 0.24 g (1.5 mmol) of 2,6-difluorobenzamide and 0.19 g (1.6 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2,6-difluorobenzoyl isocyanate in an oily state. 10 ml of fresh 1,2-dichloroethane and 0.28 g (1.5 mmol) of 2,5-dichloro-4-cyano aniline were successively added thereto, reacted for 2 hours and filtered to obtain 0.38 g (Yield 69%) of the title compound as a solid.

M.P.: 238–240° C.

$^1$H-NMR (DMSO-$d_6$, 300 MHz, ppm): δ 12.08(s,1H), 11.18 (s,1H), 8.60(s,1H), 8.37(s,1H), 7.72–7.62(m,1H), 7.32–7.26 (t,2H).

EXAMPLE 23

Preparation of 1-(2,5-dichloro-4-cyanophenyl)-3-(2-chlorobenzoyl)urea 0.23 g (1.5 mmol) of 2-chlorobenzamide and 0.19 g (1.6 mmol, 1.1 eq) of oxalyl chloride were added to 10 ml of 1,2-dichloroethane and then the mixture was stirred for 8 hours at 100° C. The reaction solution was cooled down to room temperature. The reaction solvent and excessive oxalyl chloride were removed by distillation under reduced pressure to obtain 2-chlorobenzoyl isocyanate in an oily state. 10 ml of fresh 1,2-dichloroethane and 0.28 g (1.5 mmol) of 2,5-dichloro-4-cyano aniline were successively added thereto, reacted for 2 hours and filtered to obtain 0.43 g (Yield 78%) of the title compound as a solid.

M.P.: 244–247° C.

$^1$H-NMR (DMSO-$d_6$, 300 MHz, ppm): δ 11.83(s,1H), 11.45 (s,1H), 8.64(s,1H), 8.37(s,1H), 7.68–7.43(m,4H)

The aryl benzoyl urea derivatives of the present invention prepared according to the examples as described above show an excellent pesticidal activity against pests such as diamond-back moth (*Plutella xylostella*), Tobacco cutworm (*Spodoptera litura*), and the like. Their pesticidal activity can be determined by the following experiments.

The test preparations, that is pesticidal compositions, used in the experiments hereinafter can be prepared in a variety of formulation forms according to their purposes. For convenience, the compound of the present invention was mixed with suitable amount of surfactant, water and acetone to produce a test preparation containing the test compound in a predetermined concentration in the following experiments. The compound was first tested at the concentration of 500 ppm, and then in case 100% of lethality was shown at that concentration, concentration was decreased gradually until all the pests tested were survived.

In addition, the test result at low concentrations of the compound according to the present invention was compared with that of Dimilin™ which is universally used, in order to confirm the strong pesticidal activity of the present invented compound.

EXPERIMENT 1

Test for Pesticidal Activity Against Diamond-Back Moth (*Plutella xylostella*)

Fresh cabbage leaves were cut off in the form of a round disk having a diameter of 5 cm. 25 mg of the test compound was dissolved in 50 ml of a mixture containing acetone and triton-X 100 in the ratio of 1:9 to produce a test preparation containing the test compound in the concentration of 500 ppm. Cabbage leaf disks as prepared above were treated by being dipped into the test preparation for 30 seconds and then dried in a hood. The dried cabbage leaf disks were put into a disposable petri dish having a diameter of 5 cm and then 20 three-aged larvae of diamond-back moth (*Plutella xylostella*) were inoculated thereto using a fine brush. Then, the dish was tightly closed with a lid to prevent the escape of larvae.

The petri dish with its contents was maintained at 25° C. under 60% humidity. After 120 hours, abnormal growth and lethality of *Plutella xylostella* were examined.

The efficacy of the test compound was estimated according to the following criterion and their controlling effect at a concentration of 500 ppm are described in the following Table 2.

5: 95% to 100% control value
4: 80% to less than 95% control value
3: 50% to less than 80% control value
2: 30% to less than 50% control value
1: 10% to less than 30% control value
0: less than 10% control value

TABLE 2

Pesticidal activity against Diamond-back Moth (*Plutella xylostella*)

| Test compound | Control value 500 ppm |
|---|---|
| Compound of | |
| Example 1 | 4 |
| Example 2 | 1 |
| Example 3 | 1 |
| Example 4 | 2 |
| Example 5 | 1 |
| Example 6 | 5 |
| Example 7 | 3 |
| Example 8 | 1 |
| Example 9 | 1 |
| Example 10 | 1 |
| Example 11 | 4 |
| Example 12 | 1 |

TABLE 2-continued

Pesticidal activity against Diamond-back Moth (*Plutella xylostella*)

| Test compound | Control value 500 ppm |
|---|---|
| Example 13 | 1 |
| Example 14 | 5 |
| Example 15 | 5 |
| Example 16 | 5 |
| Example 17 | 5 |
| Example 18 | 5 |
| Example 19 | 5 |
| Example 20 | 4 |
| Example 21 | 3 |
| Example 22 | 5 |
| Example 23 | 4 |

Concentration-dependent lethality (%) against diamond-back moth of some compounds among those described in Table 2 was determined and compared with that of control compound, Dimilin™, and the results are described in the following Table 3.

TABLE 3

| Test Com. | Concentration (ppm) -dependent lethality (%) | | | | | | | | |
|---|---|---|---|---|---|---|---|---|---|
| | 500 | 250 | 63 | 16 | 4 | 1 | .25 | .063 | .016 |
| Dimilin | 100 | 80 | 0 | | | | | | |
| EX.1 | 100 | 100 | 80 | 60 | 0 | | | | |
| EX.14 | 100 | 100 | 100 | 100 | 95 | 40 | | | |
| EX.15 | 100 | 100 | 100 | 100 | 100 | 100 | 100 | 50 | |
| EX.16 | 100 | 100 | 100 | 30 | | | | | |
| EX.17 | 100 | 100 | 100 | 100 | 100 | 55 | 10 | | |
| EX.18 | 100 | 100 | 100 | 100 | 100 | 95 | 75 | 50 | 20 |

EXPERIMENT 2

Test for Pesticidal Activity Against Tobacco Cutworm (*Spodoptera litura*)

Fresh cabbage leaves were cut off in the form of round disk having a diameter of 5 cm. 25 mg of the test compound was dissolved in a mixture containing acetone and triton-X 100 in a ratio of 1:9 to produce a test preparation having the test compound in a concentration of 500 ppm. The cabbage leaf disks as prepared above were treated by being dipped into the test preparation for 30 seconds and then dried in a hood. The dried cabbage leaf disks were put into a disposable petri dish having a diameter of 5 cm and then 20 three-aged larvae of Tobacco cutworm (*Spodoptera litura*) were inoculated thereto by using a fine brush. Then, the dish was tightly closed with a lid to prevent the escape of larvae.

The petri dish with its contents was maintained at 25° C. under 60% humidity. After 120 hours, abnormal growth and lethality of Tobacco cutworm were examined.

The efficacy of the test compound was estimated according to the criterion as represented in Experiment 1 above and their controlling effect at a concentration of 500 ppm are described in the following Table 4.

TABLE 4

Pesticidal activity against Tobacco cutworm (*Spodoptera litura*)

| Test compound | Control value 500 ppm |
|---|---|
| Compound of | |
| Example 1 | 5 |
| Example 2 | 5 |
| Example 3 | 5 |
| Example 4 | 3 |
| Example 5 | 1 |
| Example 6 | 2 |
| Example 7 | 3 |
| Example 8 | 4 |
| Example 9 | 1 |
| Example 10 | 4 |
| Example 11 | 4 |
| Example 12 | 2 |
| Example 13 | 1 |
| Example 14 | 5 |
| Example 15 | 5 |
| Example 16 | 5 |
| Example 17 | 5 |
| Example 18 | 5 |
| Example 19 | 5 |
| Example 20 | 3 |
| Example 21 | 3 |
| Example 22 | 5 |
| Example 23 | 4 |

Concentration-dependent lethality (%) against Tobacco cutworm of some compounds among those described in Table 4 was determined and compared with that of control compound. The results are described in the following Table 5.

TABLE 5

| Test Com. | Concentration(ppm)-dependent lethality (%) | | | | | | | | |
|---|---|---|---|---|---|---|---|---|---|
| | 500 | 250 | 63 | 16 | 4 | 1 | .25 | .063 | .016 | .008 |
| Dimilin | 100 | 100 | 100 | 90 | 50 | 0 | | | | |
| EX. 1 | 100 | 100 | 100 | 100 | 100 | 100 | 100 | 50 | 30 | |
| EX. 2 | 100 | 100 | 100 | 100 | 100 | 40 | | | | |
| EX. 3 | 100 | 100 | 100 | 100 | 100 | 100 | 40 | | | |
| EX. 14 | 100 | 100 | 100 | 100 | 100 | 85 | 45 | | | |
| EX. 15 | 100 | 100 | 100 | 100 | 100 | 100 | 100 | 95 | 55 | 5 |
| EX. 16 | 100 | 100 | 100 | 100 | 100 | 100 | 55 | 30 | | |
| EX. 17 | 100 | 100 | 100 | 100 | 100 | 100 | 100 | 75 | 15 | 15 |

As can be seen from the above results, aryl benzoyl urea derivative according to the present invention exhibits- a superior pesticidal effect especially against diamond-back moth and tobacco cutworm more than 100 to 500 times to Dimilin which is the existing inhibitor for chitin formation. Furthermore, the process for preparing the compound of the present invention is simpler than that for preparing the existing benzoyl ureido diphenyl ether derivative, therefore the present invented compound has the advantage of being obtained much more economically.

We claim:

1. An aryl benzoyl urea derivative represented by the following formula (I):

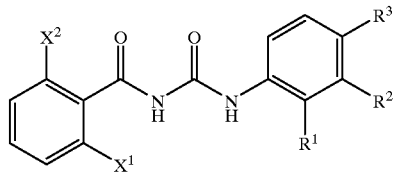

in which $X^1$ and $X^2$ independently of one another represent hydrogen, fluoro or chloro, $R^1$ represents chloro, $R^2$ represents trifluoromethyl, and $R^3$ represents fluoro.

2. The aryl benzoyl urea derivative of claim 1, wherein the compound of formula (I) is 1-(2-chloro-4-fluoro-3-trifluoromethylphenyl)-3-(2,6-difluorobenzoyl)urea.

3. The aryl benzoyl urea derivative of claim 1, wherein the compound of formula (I) is 1-(2-chloro-4-fluoro-3-trifluoromethylphenyl)-3-(2-fluorobenzoyl)urea.

4. The aryl benzoyl urea derivative of claim 1, wherein the compound of formula (I) is 1-(2-chloro-4-fluoro-3-trifluoromethylphenyl)-3-(2-chlorobenzoyl)urea.

5. A pesticidal composition comprising as an active ingredient an aryl benzoyl urea derivative represented by the following formula (I):

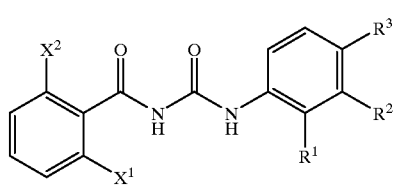

in which
$X^1$, $X^2$, $R^1$, $R^2$, and $R^3$ are defined as described in claim 1, in combination with an agriculturally acceptable carrier.

* * * * *